United States Patent
Chung et al.

(10) Patent No.: US 12,307,678 B2
(45) Date of Patent: May 20, 2025

(54) SYSTEM AND METHOD FOR SEGMENTATING BRAIN IN MRI IMAGES

(71) Applicants: GACHON UNIVERSITY OF INDUSTRY-ACADEMIC COOPERATION FOUNDATION, Seongnam-si (KR); GIL MEDICAL CENTER, Incheon (KR)

(72) Inventors: Jun Young Chung, Seoul (KR); Young Noh, Seoul (KR); Woo-Ram Kim, Incheon (KR)

(73) Assignees: GACHON UNIVERSITY OF INDUSTRY-ACADEMIC COOPERATION FOUNDATION, Seongnam-si (KR); GIL MEDICAL CENTER, Incheon (KR)

( * ) Notice: Subject to any disclaimer, the term of this patent is extended or adjusted under 35 U.S.C. 154(b) by 322 days.

(21) Appl. No.: 18/072,907

(22) Filed: Dec. 1, 2022

(65) Prior Publication Data
US 2023/0394674 A1 Dec. 7, 2023

(30) Foreign Application Priority Data
Jun. 7, 2022 (KR) .................. 10-2022-0069053

(51) Int. Cl.
*G06T 7/143* (2017.01)
*G06T 7/33* (2017.01)
*G16H 30/40* (2018.01)

(52) U.S. Cl.
CPC .............. *G06T 7/143* (2017.01); *G06T 7/337* (2017.01); *G16H 30/40* (2018.01);
(Continued)

(58) Field of Classification Search
USPC ........................................................ 382/131
See application file for complete search history.

(56) References Cited

U.S. PATENT DOCUMENTS 6,430,430 B1 * 8/2002 Gosche .................. G06T 7/155
128/923
6,591,004 B1 * 7/2003 VanEssen ............... G06T 17/00
378/4
(Continued)

FOREIGN PATENT DOCUMENTS

CN 110458869 A 11/2019
CN 110840468 A 2/2020
(Continued)

OTHER PUBLICATIONS

European Search Report for a corresponding European Patent Application.

*Primary Examiner* — Chineyere Wills-Burns
*Assistant Examiner* — Aaron Timothy Bonansinga
(74) *Attorney, Agent, or Firm* — You & IP, LLC

(57) ABSTRACT

Proposed is a system and method for segmentating brain in MRI images. According to an embodiment, it is possible to overcome limitations that gray matter is estimated to be smaller than the actual size in brain segmentation performed for quantitative analysis of a brain imaged by a magnetic resonance imaging (MRI) scanner and to accurately segment brain images by distinguishing dura mater and veins around the cerebellum by removing a large amount of cranial dura mater, thereby improving accuracy of brain quantitative analysis results and fundamentally increasing diagnostic accuracy for brain lesions.

10 Claims, 7 Drawing Sheets

(52) U.S. Cl.
CPC ............... *G06T 2207/10088* (2013.01); *G06T 2207/20132* (2013.01); *G06T 2207/30016* (2013.01)

(56) References Cited

U.S. PATENT DOCUMENTS

| | | | |
|---|---|---|---|
| 11,810,291 B2* | 11/2023 | Liu | G06T 7/11 |
| 2008/0292194 A1* | 11/2008 | Schmidt | G06T 7/0012 |
| | | | 382/131 |
| 2010/0284595 A1* | 11/2010 | Mori | G06T 7/30 |
| | | | 600/410 |
| 2014/0226890 A1* | 8/2014 | O'Brien | G01R 33/5608 |
| | | | 382/131 |
| 2019/0033418 A1* | 1/2019 | Haacke | G01R 33/50 |
| 2019/0148021 A1* | 5/2019 | Styner | G06N 20/10 |
| | | | 705/2 |
| 2020/0020098 A1* | 1/2020 | Odry | G06T 7/0012 |
| 2020/0074214 A1* | 3/2020 | Boespflug | G06V 10/267 |
| 2021/0082113 A1* | 3/2021 | Jara | A61B 5/055 |
| 2022/0354579 A1* | 11/2022 | Dyer | A61B 34/25 |

FOREIGN PATENT DOCUMENTS

| | | |
|---|---|---|
| JP | 2018-509216 A | 4/2018 |
| KR | 10-1718130 B1 | 3/2017 |
| KR | 10-2019-0105452 A | 9/2019 |
| KR | 10-2020-0007244 A | 1/2020 |
| WO | 2016-160094 A1 | 10/2016 |
| WO | 2019136745 A1 | 7/2019 |

* cited by examiner

SYSTEM AND METHOD FOR SEGMENTATING BRAIN IN MRI IMAGES

CROSS REFERENCE TO RELATED APPLICATION

The present application claims priority to Korean Patent Application No. 10-2022-0069053, filed Jun. 7, 2022, the entire contents of which is incorporated herein for all purposes by this reference.

BACKGROUND OF THE INVENTION

Field of the Invention

The present disclosure relates to a system and method for segmentating a brain in magnetic resonance imaging (MRI) images and, more particularly, to a technique that enables quantitative analysis of the brain by segmenting the brain into components in 3D T1 MRI images.

Description of the Related Art

For quantitative analysis of brain anatomy, a typical brain segmentation tool adopts a method of accurately extracting brain and non-brain structures before preprocessing, and from a preprocessed image, only brain parts are extracted and segmented through non-linear registration to a predetermined template.

Such brain segmentation tool segments a brain in images obtained by 3D T1 magnetic resonance imaging (MRI) without dura mater surrounding the brain and veins around the cerebellum being removed, and thus the dura mater and the veins around the cerebellum that are not removed are recognized as brain. As a result, large errors occur in quantitative analysis regarding cerebral thickness and volume, etc. and errors occur during calculation of cerebellar volume, etc.

Therefore, errors occur in quantitative analysis of MRI images which is the basis for prevention, diagnosis and treatment of various brain diseases, as well as in quantitative analysis of standardized uptake value ration (SUVR) on brain positron emission tomography (PET) images.

Moreover, in order to minimize such errors in quantitative analysis of the brain, the segmented brain image is visually checked and corrected, and then quantitative analysis is performed again. Thus, the accuracy of the analysis result is lowered, and conducting multiple quantitative analyses wastes time and costs labor, which is problematic.

Documents of Related Art (Patent Document 0001) Korean Patent Application Publication No. 2019-0105452 (published Sep. 17, 2019)

SUMMARY OF THE INVENTION

Accordingly, the present disclosure has been made keeping in mind the above problems occurring in the related art, and the present disclosure is intended to provide a system and method for segmentating brain in magnetic resonance imaging (MRI) images, which is to fundamentally improve accuracy of quantitative analysis results of brain anatomical structures with brain images produced by an MRI scanner.

An objective of the present disclosure is to provide a system and method for segmentating brain in MRI images, which is to prevent wasting time and labor in deriving quantitative analysis results of a brain.

Objectives of the present disclosure are not limited to the above-mentioned objectives, and other objectives and advantages of the present disclosure not mentioned above may be understood by the following description and will be more clearly understood by embodiments of the present disclosure. In addition, it will be readily apparent that the objectives and advantages of the present disclosure may be realized by means of the instrumentalities and combinations indicated in the claims.

In order to achieve the above objective, according to an embodiment of the present disclosure, there is provided a system for segmentating brain in magnetic resonance imaging (MRI) images including: a brain image collection unit configured to collect a brain image produced by an MRI scanner; a preprocessing unit configured to perform preprocessing on the brain image; and a brain analysis unit configured to generate a brain probability map for each brain component for the preprocessed brain image, create a mask for each brain component based on the brain probability map generated, segment the preprocessed brain image by the each brain component using the mask created, and derive a final brain image from the segmented brain image using a final mask.

Preferably, the brain component may be at least one of gray matter, white matter, cerebrospinal fluid, ventricles, and other structures.

Preferably, the preprocessing unit may perform preprocessing on the brain image produced by the MRI scanner, and may include: an intensity processing module configured to perform bias field correction on the brain image collected to remove intensity non-uniformity arised during imaging; a neck removal module configured to remove a part below cerebellum after the bias field correction; a position adjustment module configured to adjust the brain image received from the neck removal module in a direction of a predetermined template; and a template registration module configured to perform linear or non-linear registration to the template by matching a position of the brain image to a position of the template.

Preferably, the brain analysis unit may include: a brain probability map generation module configured to generate the brain probability map for the each brain component using a probability map of a predetermined template for the preprocessed brain image; a mask creation module configured to create the mask for the each brain component on the basis of the brain probability map each generated for the each brain component; a brain image segmentation module configured to derive the segmented brain image by acquiring the each brain component in the preprocessed brain image using the mask each created for the each brain component; and a final brain image derivation module configured to derive the final brain image from the segmented brain image and derived using the final mask.

Preferably, the brain image segmentation module may include: a first mask creator configured to create a first mask on the basis of a white matter mask, a gray matter mask, a ventricular mask, and an other structure mask for acquiring other brain components, among the white matter mask, the gray matter mask, a cerebrospinal fluid mask, the ventricular mask, and the other structure mask, created for the each brain component; a first dura remover configured to primarily remove cranial dura mater including dura mater near an orbitofrontal region on a lateral side of the white matter after acquiring a brain image including a white matter, gray matter, and ventricles from the preprocessed brain image using the first mask and binarizing and eroding the brain image acquired; a brain image enlarger configured to acquire a brain image of enlarged gray matter through secondary dilation after primarily dilating the brain image which includes a white matter, gray matter, and ventricles and in which the cranial dura mater is primarily removed in order to restore the eroded brain image; a second mask creator configured to create a second mask by multiplying the first mask and the cerebrospinal fluid mask, and acquire the gray matter containing a portion of the cerebrospinal fluid from the brain image of enlarged gray matter using the second mask created; a gray matter acquirer configured to acquire a brain image of gray matter through dilation and erosion after combining the brain image including a white matter, gray matter, and ventricles acquired through erosion and dilation of the brain image which includes a white matter, gray matter, and ventricles and in which the cranial dura mater is primarily removed with the brain image of enlarged gray matter; a second dura remover configured to secondarily remove the cranial dura mater after acquiring a brain image by subtracting the other structures from the brain image of gray matter, and then eroding and dilating the brain image acquired; and a segmented brain image acquirer configured to acquire a segmented brain image in which structures other than the white matter, gray matter, cerebrospinal fluid, and ventricles are removed by post-processing to fill a hole in the brain image from the second dura remover.

Preferably, the final brain image derivation module may be provided to create the final mask in combination of masks for the each brain component, and derive the final brain image, in which cranial dura mater and a part below cerebellum are removed, from the segmented brain image and the preprocessed brain image using the final mask.

Preferably, the first mask may be provided to remove a brain image acquired using an other structure mask after multiplying a brain image of gray matter acquired using a gray matter mask by a constant greater than 1, and combining a brain image of a white matter acquired using a white mask with a brain image of ventricles acquired using a ventricular mask.

According to another embodiment of the present disclosure, there is provided a method for segmentating brain in MRI images, performed by the brain analysis unit of claim 1 and for segmenting a preprocessed brain image by each brain component by combining masks for respective brain components created using brain probability maps for the respective brain components. The method includes: first mask creating to create a first mask based on the masks created for the respective brain components; first dura removing to primarily remove cranial dura mater including dura mater near an orbitofrontal region on a lateral side of a white matter after acquiring a brain image including the white matter, a gray matter, and ventricles from a preprocessed brain image using the first mask and binarizing and eroding the brain image acquired; brain image enlarging to acquire a brain image B of enlarged gray matter through secondary dilation after primarily dilating the brain image A which includes the white matter, gray matter, and ventricles and in which the cranial dura mater is primarily removed in order to restore the eroded brain image; second mask creating to create a second mask by multiplying the first mask and a cerebrospinal fluid mask, and acquire a brain image C of gray matter containing a portion of cerebrospinal fluid from the brain image B of enlarged gray matter using the second mask created; gray matter acquiring to acquire a brain image F of gray matter through dilation and erosion after combining a brain image D including the white matter, gray matter, and ventricles acquired through erosion and dilation of the brain image C which includes the white matter, gray matter, and ventricles and in which the cranial dura mater is primarily removed with the brain image C of enlarged gray matter; second dura removing to secondarily remove the cranial dura mater after acquiring a brain image G by subtracting other structures from the brain image F of gray matter, and then eroding and dilating the brain image G acquired; and segmented brain image acquiring to acquire a segmented brain image I in which structures other than the white matter, gray matter, cerebrospinal fluid, and ventricles are removed by post-processing to fill a hole in a brain image H from the second dura removing.

Preferably, the method for segmentating brain in MRI images may further include: final brain image deriving to create a final mask by combining the masks for the respective brain components, and acquire a final brain image J, in which the cranial dura mater and a part below cerebellum are removed, from the segmented brain image I acquired and the preprocessed brain image using the final mask created.

As described above, according to a system and method for segmentating brain in MRI images of the present disclosure, it is possible to overcome limitations that gray matter is estimated to be smaller than the actual size in brain segmentation performed for quantitative analysis of a brain imaged by a magnetic resonance imaging (MRI) scanner and to accurately segment brain images by distinguishing dura mater and veins around the cerebellum by removing a large amount of cranial dura mater, thereby improving accuracy of brain quantitative analysis results and fundamentally increasing diagnostic accuracy for brain lesions.

BRIEF DESCRIPTION OF THE DRAWINGS

The following drawings accompanying this specification illustrate preferred embodiments of the present disclosure, and serve to further understand the technical idea of the present disclosure together with the detailed description of the disclosure to be described later. Therefore, the present disclosure should not be construed as being limited only to the matters described in the drawings.

DETAILED DESCRIPTION OF THE INVENTION

Figure 1:
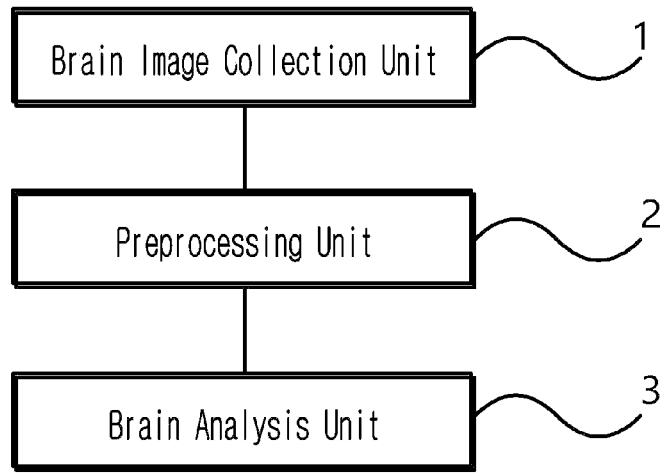
FIG. 1 is a block diagram of a system for segmentating brain in MRI images according to an embodiment of the present disclosure.

Hereinafter, preferred embodiments of a system and method for segmentating brain in MRI images of the present disclosure will be described with reference to the accompanying drawings.

Advantages and features of the present disclosure, and methods for achieving them, will become clear with reference to the embodiments described below in conjunction with the accompanying drawings. However, the present disclosure is not limited to the embodiments disclosed below and may be implemented in various different forms. These embodiments are provided only to complete the disclosure of the present disclosure and to completely inform those skilled in the art of the scope of the disclosure to which the present disclosure belongs. The present disclosure is only defined by the scope of the claims.

The teams used in this specification will be briefly described, and the present disclosure will be described in detail.

Although the terms used in the present disclosure have been selected from general terms that are currently widely used as much as possible while considering the functions in the present disclosure, they may vary depending on the intention of a person skilled in the art or a case law, the emergence of new technologies, and the like. In addition, in certain cases, there are also terms arbitrarily selected by the applicant, and in this case, their meanings will be described in detail in the corresponding description. Thus, any term used in the present disclosure should be defined based on the meaning of the term and the overall content of the present disclosure, not simply the name of the term.

In the entire specification, when a component is said to "comprise" or "include" a certain component, it means that it may further include other components, not excluding other components unless otherwise stated.

Therefore, functionality provided within components and "parts" may be combined into fewer components and "parts" or further separated into additional components and "parts".

Hereinafter, with reference to the accompanying drawings, embodiments of the present disclosure will be described in detail so that those skilled in the art may easily carry out the present disclosure. In order to clearly describe the present disclosure in the drawings, parts irrelevant to the description are omitted.

For each component to which an embodiment is applied, any number may be included in any appropriate configuration. In general, computing and communication systems come in a wide variety of configurations, and the drawings do not limit the scope of the present disclosure to any particular configuration. Although the drawings illustrate one operating environment in which various features disclosed in this patent document may be used, such features may be used in any other suitable system.

According to an embodiment, from 3D T1 brain images obtained by magnetic resonance imaging (MRI), by acquiring a brain image with dura mater removed and gray matter accurately included using respective masks created for brain components based on respective brain probability maps for brain components, accuracy of brain quantitative analysis of brain components may be improved.

Figure 2:
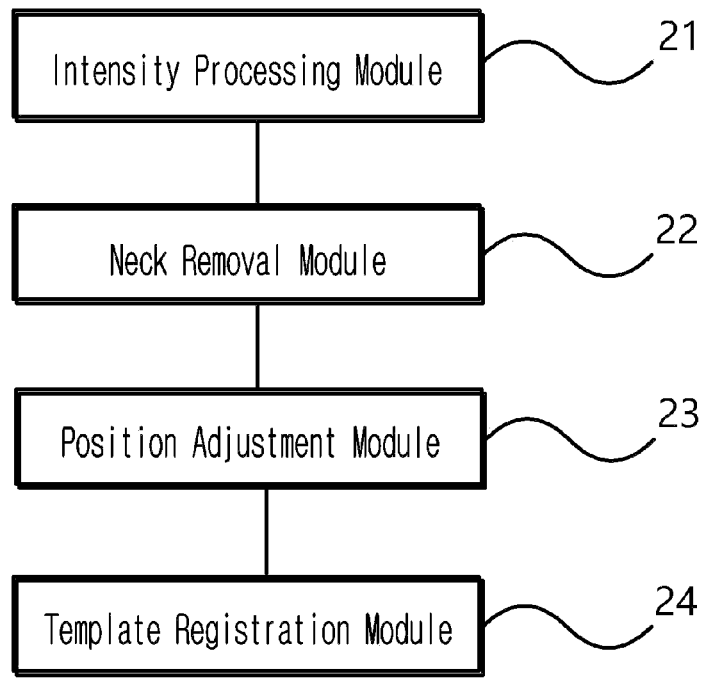
FIG. 2 is a detailed configuration diagram of a preprocessing unit shown in FIG. 1.
Figure 3:
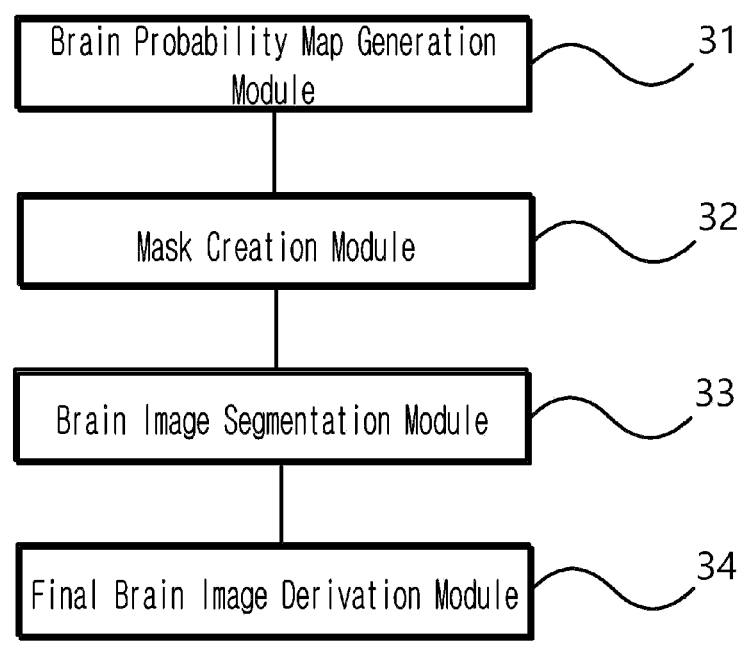
FIG. 3 is a detailed configuration diagram of a brain analysis unit shown in FIG. 1.
Figure 4:
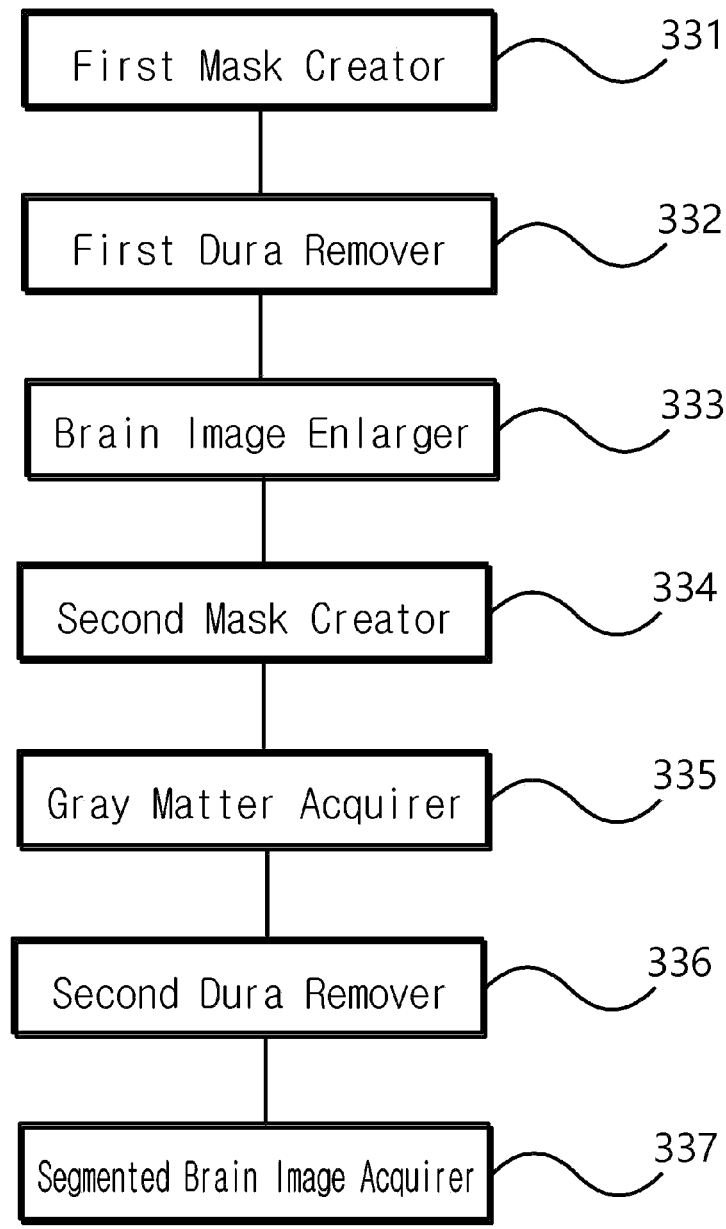
FIG. 4 is a detailed configuration diagram of a brain image segmentation module shown in FIG. 3.
Figure 5:
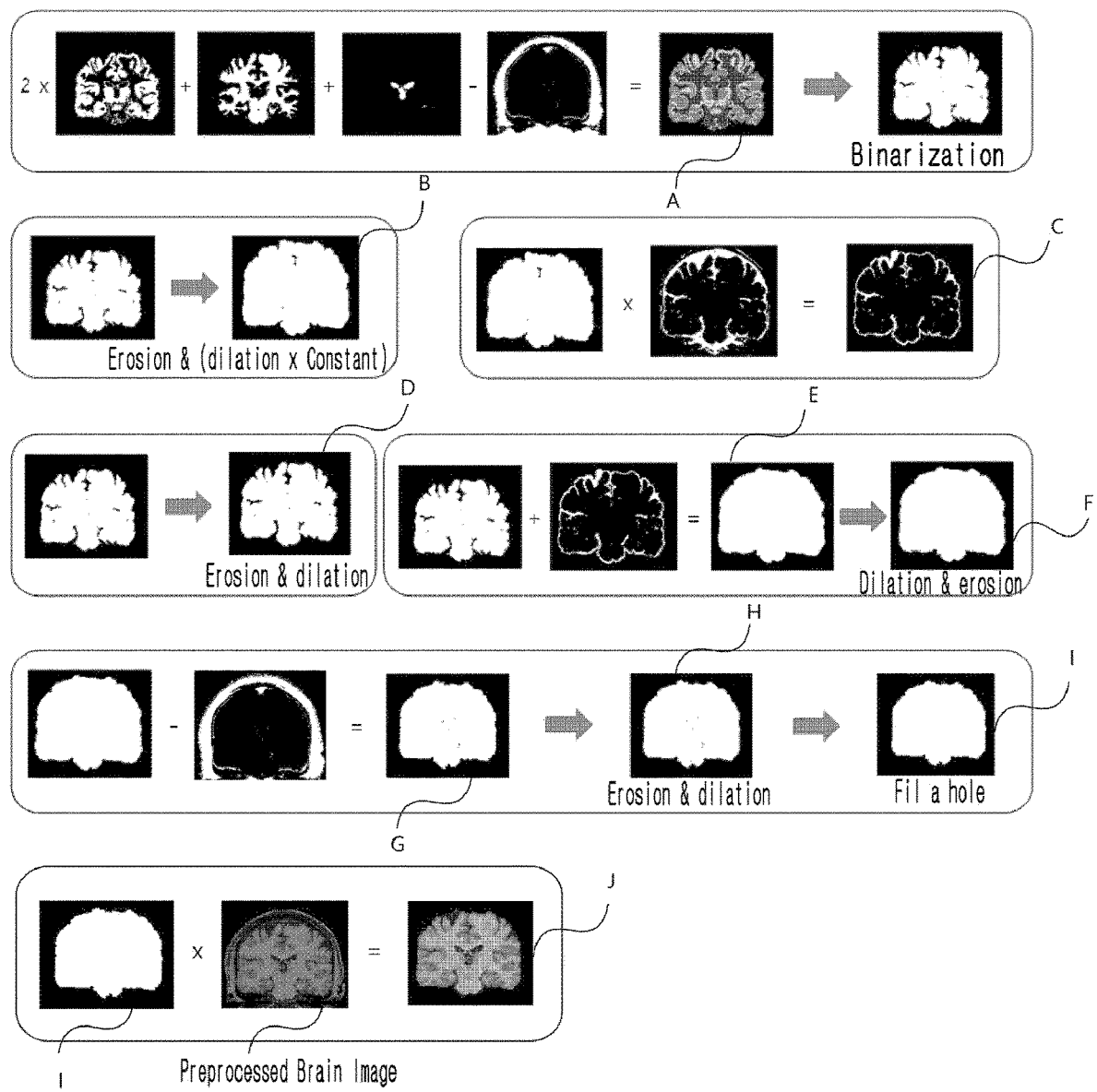
FIG. 5 is an exemplary diagram showing brain images output from the brain image segmentation module shown in FIG. 4.

FIG. 1 is a block diagram of a system for segmentating brain in MRI images according to an embodiment, FIG. 2 is a detailed configuration diagram of a preprocessing unit shown in FIG. 1, FIG. 3 is a detailed configuration diagram of a brain analysis unit shown in FIG. 1, FIG. 4 is a detailed configuration diagram of a brain image segmentation module shown in FIG. 3, and FIG. 5 is an exemplary diagram showing brain images output from the brain image segmentation module shown in FIG. 4.

Referring to FIGS. 1 to 5, from 3D T1 images obtained by MRI, a final brain image with the cranial dura mater is removed and containing gray matter of the same size as the actual measurement is obtained by using a mask created for each brain component based on a brain probability map for each brain component.

That is, referring to FIG. 1, a system for segmentating brain in MRI images according to an embodiment includes a brain image collection unit 1, a preprocessing unit 2, and a brain analysis unit 3. The brain image collection unit 1 collects 3D T1 images obtained by MRI in a time-sequential manner. At this time, by using 3D T1 images obtained by MRI, a quantitative analysis of brain anatomy is performed.

To this end, the preprocessing unit 2 performs bias field correction on the collected brain image to remove intensity non-uniformity, and performs linear or non-linear registration to match the position of the brain image with the position of a predetermined template. Referring to FIG. 2, the preprocessing unit 2 includes an intensity processing module 21, a neck removal module 22, a position adjustment module 23, and a template registration module 24. At this time, the template may include a pre-built template or a newly created template.

The intensity processing module 21 removes the intensity non-uniformity, arised during imaging, of the collected brain images through a non-parametric non-uniform intensity normalization algorithm. As an example, bias field correction using non-parametric non-uniform intensity normalization algorithm uses B-spline interpolation.

In the case of B-spline interpolation, when correcting the curve of a patch, if one point is corrected, the curve of the desired area is modified. Thus, the bias field correction using this non-spline satisfies the following Equation 1.

$$v(x)=u(x)f(x)+n(x) \qquad \text{[Equation 1]}$$

Here, v(x) is a given brain image, u(x) is an undamaged image, f(x) is a bias field, and n(x) is noise.

Assuming that there is no noise n(x) from Equation 1, the log-likelihood objective function for a given brain image may be expressed as Equation 2 below.

$$\hat{v}(x)=\hat{u}(x)+\hat{f}(x) \text{ Here, } \hat{u}=\log u \qquad \text{[Equation 2]}$$

By solving the log-likelihood objective function, the converging value of the bias field in Equation 1 is derived.

That is, the solution of the log-likelihood objective function may be derived from Equation 3, and the converging estimate of the bias field may be derived from Equation 4.

$$\hat{u}^1 = \hat{v} - \hat{f}_r^1 \qquad \text{[Equation 3]}$$

$$\hat{u}^2 = \underbrace{\left(\hat{v} - \hat{f}_r^1\right)}_{\hat{u}^1} - \hat{f}_r^2$$

$$\hat{u}^3 = \underbrace{\left(\left(\hat{v} - \hat{f}_r^1\right) - \hat{f}_r^2\right)}_{\hat{u}^2} - \hat{f}_r^3$$

$$\vdots$$

$$\hat{u}^n = \hat{v} - \sum_{i=1}^{n} \hat{f}_r^i$$

$$\hat{f}_e^n = \sum_{i=1}^{n} \hat{f}_r^i \qquad \text{[Equation 4]}$$

A bias field correction is performed using this $\hat{f}_e^n$ estimate.

The brain image of the intensity processing module 21 is provided to the neck removal module 22. The removal module 22 removes neck, a part below the cerebellum, included in the brain image, and the brain image from which the neck is removed is transmitted to the position adjustment module 23.

The position adjustment module 23 adjusts the position of the brain image in the direction of a predetermined template, and the template registration module 24 performs linear registration or non-linear registration for a space where the position of the brain image and the position of the template match.

In the case of the linear registration, rigid body registration that matches the input image to the position of the template by rotation and movement without distorting the image, or affine registration that may increase or decrease the size of the image is used. The non-linear registration includes the process of linear registration, and in the case of the non-linear registration, the image is distorted according to the shape of the template and registered to the template.

At this time, by combining the matrix used for removing the neck after linear or non-linear registration to the template and the matrix used for linear registration to the template, and performing the processes of removing the neck and linear or non-linear registration at the same time, data corruption in the brain image necessary for segmentation may be prevented.

The preprocessed brain image is transmitted to the brain analysis unit 3.

Referring to FIG. 3, the brain analysis unit 3 is configured to create a mask for each brain component to identify an anatomical structure of a brain, derive a segmented brain image using the created mask for each brain component, and derive a final brain image from the derived segmented brain image and preprocessed image. The brain analysis unit 3 includes a brain probability map generation module 31, a mask creation module 32, a brain image segmentation module 33, and a final brain image derivation module 34. At this time, the brain component includes white matter, gray matter, cerebrospinal fluid, ventricles, and other structures. The other structures refer to brain structures other than white matter, gray matter, cerebrospinal fluid, and ventricles.

The brain probability map generation module 31 generates a brain probability map for each brain component using a probability map of the predetermined template or an updated template for the preprocessed brain image.

That is, the brain probability map is generated by calculating the probability that white matter, gray matter, cerebrospinal fluid, ventricles, and other structures exist in each voxel of the input image by using the probability map template and the input 3D T1 MR images. At this time, the brain probability map may be modeled with Mixture of Gaussians (hereinafter refer to as MOG).

For example, for univariate data, the kth Gaussian is modeled as mean ($\mu_k$), variance ($\sigma_k^2$), and mixing ration ($\gamma_k$), and assuming that MOG belongs to the kth Gaussian ($c_{j=}k$) and that the kth Gaussian has mean ($\mu_k$) and variance ($\sigma_k^2$) as parameters, the probability of obtaining data with intensity $y_i$ may be derived from Equation 5 below.

$$P(y_i \mid c_i = k, \mu_k, \sigma_k) = \frac{1}{(2\pi\sigma_k^2)^{\frac{1}{2}}} \exp\left(-\frac{(y_i - \mu_k)^2}{2\sigma_k^2}\right) \quad \text{[Equation 5]}$$

Applying this probability to the brain probability map, the probability of brain structure k for voxel i of the brain image satisfies the following equation 6. At this time, the brain probability map registered in the template is derived by the parameter α.

$$P(c_i = k \mid \gamma, \alpha) = \frac{\gamma_k b_{ik}(\alpha)}{\sum_{j=1}^{K} \gamma_j b_{ij}(\alpha)} \quad \text{[Equation 6]}$$

When the generated brain probability map is an element corresponding to each template, it is a value of 1 or less. Thus, the mask creation module 32 creates a mask for the binarized brain probability map by binarizing the brain probability map with a predetermined threshold.

The brain image segmentation module 33 derives segmented brain image by combining individual masks for white matter, gray matter, cerebrospinal fluid, ventricles, and other structures into one and segmenting the preprocessed brain image, and the final brain image derivation module 34 derives a final brain image with the dura mater and the part below the cerebellum removed from the derived segmented brain image and preprocessed brain image using a final mask created by combining individual masks for brain components into one.

The brain image segmentation module 33 is configured to derive the segmented brain image from the preprocessed brain image using the masks for the white matter, gray matter, cerebrospinal fluid, ventricles, and other structures. Referring to FIGS. 4 and 5, the brain image segmentation module 33 may include at least one of a first mask creator 331, a first dura remover 332, a brain image enlarger 333, a second mask creator 334, a gray matter acquirer 335, a second dura remover 336, and a segmented brain image acquirer 337.

The first mask creator 331 creates a first mask on the basis of a white matter mask, a gray matter mask, a ventricular mask, and an other structure mask for acquiring other brain components, among the white matter mask, the gray matter mask, a cerebrospinal fluid mask, the ventricular mask, and the other structure mask, created for the each brain component.

The first dura remover 332 acquires a brain image A including white matter, gray matter, and ventricles from the preprocessed brain image using the first mask, and then binarizes the acquired brain image A. As such, the dura mater included in the preprocessed brain image is primarily removed.

At this time, the brain image A is derived by multiplying the gray matter brain image acquired using the gray matter mask by a constant greater than 1, adding the white matter brain image acquired using the white matter mask and the ventricular brain image acquired using the ventricular mask, and subtracting the structure brain image acquired using the other structure mask. Here, the constant greater than 1 is set as the result value obtained through a number of experiments, which makes it possible to acquire an optimal brain image.

The primarily removed dura mater includes the dura mater near the orbitofrontal region on the lateral side of the white matter, and the brain image A is transmitted to the brain image enlarger 333.

The brain image enlarger 333 erodes the brain image A and primarily dilates the eroded brain image A to restore the eroded brain image A, and then secondarily dilates the restored brain image A to acquire an enlarged gray matter brain image B. The enlarged gray matter brain image B is transmitted to the second mask creator 334.

The second mask creator 334 creates a second mask by multiplying the first mask and the cerebrospinal fluid mask, and derives a brain image C by acquiring gray matter including a part of cerebrospinal fluid from the enlarged gray matter brain image B using the created second mask.

Meanwhile, the gray matter acquirer 335 acquires a brain image D through erosion and dilation of the binarized brain image A after primary removal of the dura mater, acquires a brain image E by combining the acquired brain image D and the brain image C acquired using the second mask, and acquires a brain image F of the gray matter by sequentially dilating and eroding the acquired brain image E.

The second dura remover 336 acquires a brain image G from which other structures except for white matter, gray matter, cerebrospinal fluid, and ventricles are removed from the gray matter brain image F, and acquires a brain image H in which the dura mater is secondarily removed through erosion and dilation of the acquired brain image G.

The segmented brain image acquirer 337 outputs a brain image I by performing post-processing to fill in the hole of the brain image H from which the dura mater is secondarily removed, and derives the brain image I in which each brain component is segmented.

The final brain image derivation module 34 acquires a final brain image J, in which the cranial dura mater and the part below the cerebellum removed, from the brain image I and the preprocessed brain image using a final mask. At this time, the final mask is created from a combination of the gray matter mask, white matter mask, cerebrospinal fluid mask, ventricular mask, and other structure mask. In addition, the final brain image J includes white matter, gray matter, cerebrospinal fluid, ventricles, and other structures with the cranial dura mater and veins around the cerebellum removed.

Figure 6A:
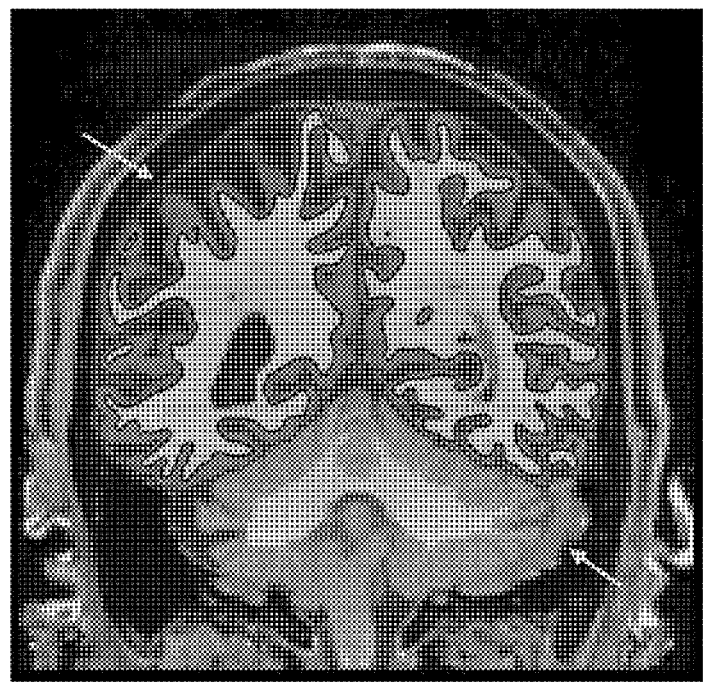
FIG. 6A to 6C are views showing quantitative analysis results on segmented brain images according to the embodiment of the present disclosure and related art technology.
Figure 6B:
Figure 6C:
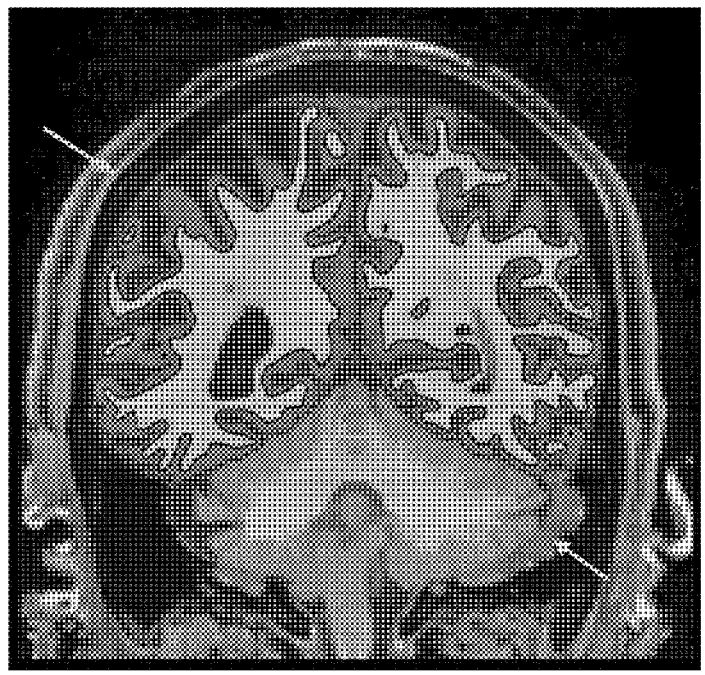

FIG. 6A is a view showing a typical quantitatively analyzed brain image, FIG. 6B is a view showing a brain image quantitatively analyzed according to an embodiment of the present disclosure, and FIG. 6C is a view showing a brain image re-quantitatively analyzed after directly correcting an error with the measured brain through visual inspection during quantitative analysis. Referring to FIGS. 6A to 6C, it can be confirmed that, in the brain image quantitatively analyzed according to the conventional method, the dura mater and the veins around cerebellum are misclassified into the cerebellum, and when comparing the brain image of 6A with the brain image of 6B which is quantitatively analyzed according to the embodiment of the present disclosure and the brain image of 6C which is quantitatively analyzed through visual inspection and correction, it can be confirmed that the dura mater and the veins around cerebellum are accurately removed in the brain image of 6B and the brain image of 6C.

According to the embodiment, in brain image segmentation performed for quantitative analysis of the brain imaged by an MRI scanner, by accurately removing the cranial dura mater and the veins below the cerebellum, brain images may be accurately segmented as the dura mater and veins around the cerebellum are distinguished, thereby improving accuracy of brain quantitative analysis results and fundamentally increasing diagnostic accuracy for brain lesions.

Figure 7:
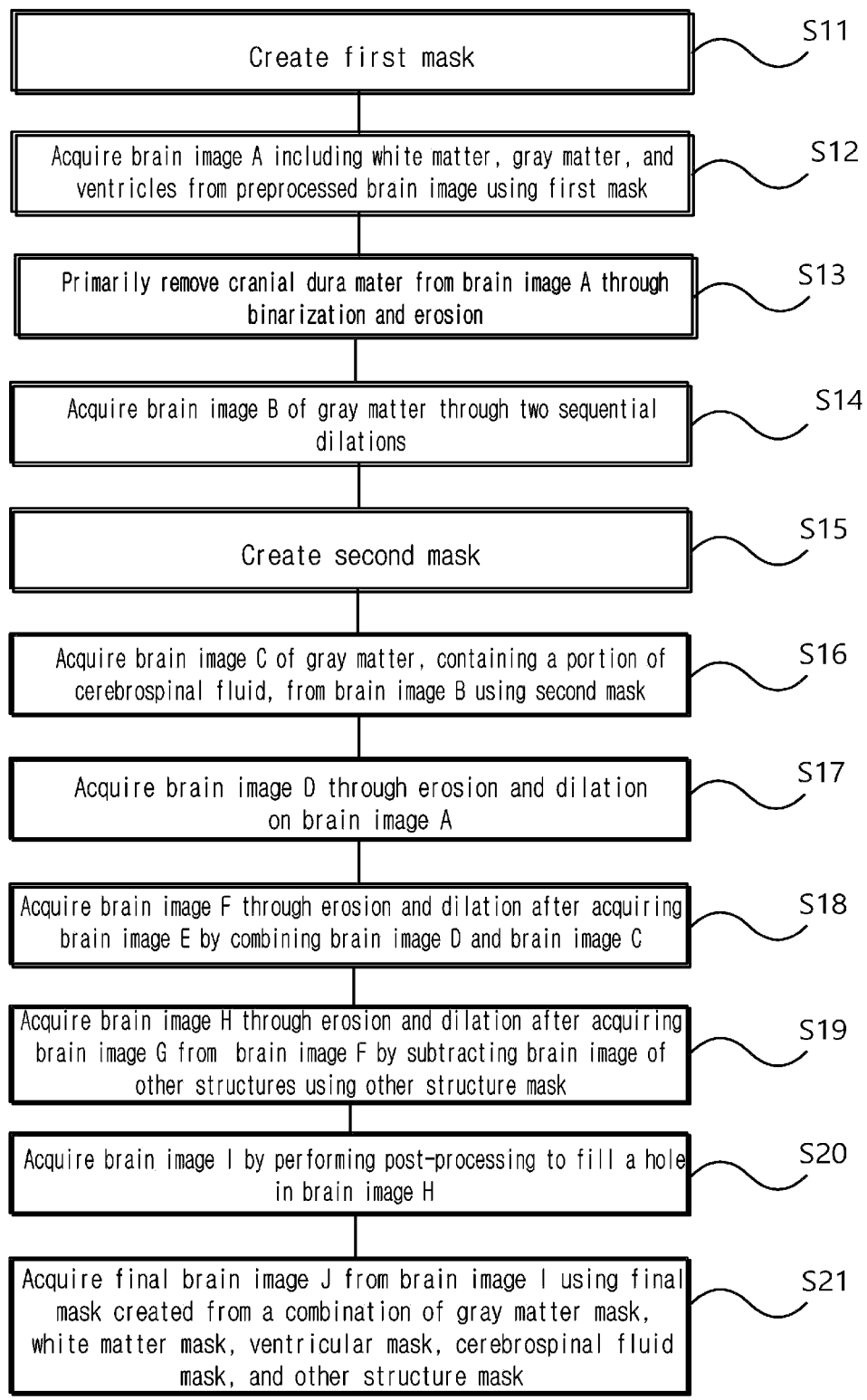
FIG. 7 is a flow chart showing a method for segmentating brain in MRI images according to another embodiment of the present disclosure.

FIG. 7 is a flow chart showing a method for segmentating brain in MRI images, performed by the brain analysis unit of FIG. 3. Referring to FIGS. 5 and 7, the method for segmentating brain in MRI images according to another embodiment of the present disclosure will be described.

In step S11, the brain analysis unit 3 of the embodiment creates the first mask based on respective masks created for the brain components. The brain component is at least one of gray matter, white matter, cerebrospinal fluid, ventricles, and other structures, and a mask is created for each brain component. The first mask is created by multiplying the gray matter mask by a constant greater than 1, adding the white matter mask and the ventricular mask, and subtracting the other structure mask.

In steps S12 and S13, the brain analysis unit 3 of the embodiment acquires the brain image A, including white matter, gray matter, and ventricles, from the preprocessed brain image based on the 3D T1 MR images using the first mask, and then erodes the acquired brain image A to primarily remove the cranial dura mater including the dura mater near the orbitofrontal region on the lateral side of the white matter.

In step S14, the brain analysis unit 3 of the embodiment restores the eroded brain image by primarily dilating the brain image B, including white matter, gray matter, and ventricles, from which the dura mater is primarily removed. The gray matter in the brain image B is enlarged through secondary dilation.

In step S15, the brain analysis unit 3 of the embodiment creates the second mask by multiplying the first mask and the cerebrospinal fluid mask, and in step S16, acquires the brain image C of the gray matter including a part of cerebrospinal fluid from the enlarged gray matter brain image B using the created second mask.

Thereafter, in steps S17 and S18, the brain analysis unit 3 of the embodiment acquires the brain image E by combining the brain image D of white matter, gray matter, and ventricles acquired by sequentially eroding and dilating the brain image A with the gray matter brain image C enlarged using the second mask, and acquires the brain image F of the gray matter by sequentially dilating and eroding the acquired brain image E.

Meanwhile, in step S19, the brain analysis unit 3 of the embodiment acquires the brain image G from which the image of other structures is removed from the gray matter brain image F acquired in step S18, and acquires the brain image H from which the cranial dura mater is secondarily removed through erosion and dilation of the acquired brain image G from which the other structures are removed.

Thereafter, in step S20, the brain analysis unit 3 of the embodiment the brain image I post-processed to fill in the hole of the brain image H from which the cranial dura mater is secondarily removed.

Meanwhile, in step S21, the brain analysis unit 3 acquires the final brain image J from the post-processed brain image I and the preprocessed brain image.

According to the embodiment, in brain segmentation performed for quantitative analysis of a brain imaged by a magnetic resonance imaging (MRI) scanner, it is possible to accurately segment brain images by distinguishing the dura mater and veins around the cerebellum by removing a large amount of cranial dura mater, thereby improving accuracy of brain quantitative analysis results and fundamentally increasing diagnostic accuracy for brain lesions.

The embodiments described above may be implemented as hardware components, software components, and/or a combination of hardware components and software components. For example, the devices, methods and components described in the embodiments may be implemented using one or more general-purpose or special-purpose computers, such as a processor, controller, arithmetic logic unit (ALU), digital signal processor, microcomputer, field programmable gate array (FPGA), programmable logic unit (PLU), microprocessor, or any other device capable of executing and responding to instructions. A processing device may execute an operating system (OS) and one or more software applications running on the operating system. In addition, the processing device may access, store, manipulate, process, and generate data in response to execution of software. For convenience of understanding, the processing device is sometimes described as one being used. However, it will be appreciated by those skilled in the art that the processing device may include multiple processing elements and/or multiple types of processing elements. For example, the processing device may include a plurality of processors or a processor and a controller. In addition, other processing configurations are also possible, such as parallel processors.

Software may include a computer program, code, instructions, or a combination of one or more of these, and may configure the processing units to operate as desired or may command the processing units independently or collectively. Software and/or data may be permanently or temporarily embodied in some type of machine, component, physical device, virtual equipment, computer storage medium or device, or signal wave being transmitted in order to be interpreted by the processing device or to provide instructions or data to the processing device. Software may be distributed on networked computer systems and stored or executed in a distributed manner. Software and data may be stored on one or more computer readable media.

The method according to the embodiment may be implemented in the form of program instructions that may be executed through various computer means and recorded on a computer readable medium. Computer readable media may include program instructions, data files, data structures, etc. alone or in combination. Program instructions recorded on the computer readable medium may be specially designed and configured for the embodiment or may be known and available to those skilled in the art of computer software. Examples of computer-readable recording media include magnetic media such as hard disks, floppy disks, and magnetic tapes, optical media such as CD-ROM and DVD, magneto-optical media such as floptical disks, and a hardware device specially configured to store and execute program instructions such as ROM, RAM, flash memory, etc. Examples of program instructions include high-level language codes that may be executed by a computer using an interpreter, etc. as well as machine language codes such as those produced by a compiler. The hardware device may be configured to act as one or more software modules to perform the operations of the embodiments and vice versa.

As described above, although the embodiments have been described with limited drawings, those skilled in the art may apply various technical modifications and variations based on the above. For example, appropriate results may be achieved even if the described techniques may be performed in an order different from that described, and/or components of the described systems, structures, devices, circuits, etc. may be combined or combined in a manner different from that described, or substituted or substituted by other components or equivalents.

What is claimed is:

1. A system for segmenting brain in magnetic resonance imaging (MRI) images, the system comprising:
   one or more hardware processors, wherein said one or more hardware processors are configured to:
   collect a brain image produced by an MRI scanner;
   perform preprocessing on the brain image;
   generate a brain probability map for each brain component using a probability map of a predetermined template for the preprocessed brain image;
   create a mask for the each brain component on the basis of the brain probability map each generated for the each brain component;
   create a first mask on the basis of a white matter mask, a gray matter mask, a ventricular mask, and a structure mask for acquiring other brain components, among the white matter mask, the gray matter mask, a cerebrospinal fluid mask, the ventricular mask, and the structure mask, created for the each brain component;
   primarily remove cranial dura mater including dura mater near an orbitofrontal region on a lateral side of a white matter after acquiring a brain image including the white matter, gray matter, and ventricles from the brain image preprocessed using the first mask and binarizing and eroding the brain image acquired;
   acquire a brain image of enlarged gray matter through secondary dilation after primarily dilating the brain image which includes the white matter, gray matter, and ventricles and in which the cranial dura mater is primarily removed in order to restore the brain image eroded;
   create a second mask by multiplying the first mask and the cerebrospinal fluid mask, and acquire the gray matter containing a portion of the cerebrospinal fluid from the brain image of enlarged gray matter using the second mask created;
   acquire a brain image of gray matter through dilation and erosion after combining the brain image including the white matter, gray matter, and ventricles acquired through erosion and dilation of the brain image which includes the white matter, gray matter, and ventricles and in which the cranial dura mater is primarily removed with the brain image of enlarged gray matter;
   secondarily remove the cranial dura mater after acquiring a brain image by subtracting the other structures from the brain image of gray matter, and then eroding and dilating the brain image acquired;
   acquire a segmented brain image in which structures other than the white matter, gray matter, cerebrospinal fluid, and ventricles are removed by post-processing to fill a hole in the brain image from the second dura remover; and
   derive a final brain image from the segmented brain image and derived using a final mask,
   wherein the brain component is at least one of gray matter, white matter, cerebrospinal fluid, ventricles, and other structures.

2. The system for segmenting brain in MRI images of claim 1, wherein said one or more hardware processors further perform preprocessing on the brain image produced by the MRI scanner, and comprises:
   performing bias field correction on the brain image collected to remove intensity non-uniformity arised during imaging;
   removing a part below cerebellum after the bias field correction;
   adjusting the brain image received from the neck removal module in a direction of a predetermined template; and
   performing linear or non-linear registration to the template by matching a position of the brain image to a position of the template.

3. The system for segmenting brain in MRI images of claim 1, wherein said one or more hardware processors are further configured to create the final mask in combination of masks for the each brain component, and derive the final brain image, in which cranial dura mater and a part below cerebellum are removed, from the segmented brain image and the preprocessed brain image using the final mask.

4. The system for segmenting brain in MRI images of claim 1, wherein the first mask is provided to remove a brain image acquired using the structure mask after multiplying a brain image of gray matter acquired using a gray matter mask by a constant greater than 1, and combining a brain image of a white matter acquired using a white mask with a brain image of ventricles acquired using a ventricular mask.

5. A method for segmenting brain in MRI images for segmenting a preprocessed brain image by each brain component by combining masks for respective brain components created using brain probability maps for the respective brain components, the method comprising:

first mask creating to create a first mask based on the masks created for the respective brain components;

first dura removing to primarily remove cranial dura mater including dura mater near an orbitofrontal region on a lateral side of a white matter after acquiring a brain image including the white matter, a gray matter, and ventricles from a preprocessed brain image using the first mask and binarizing and eroding the brain image acquired;

brain image enlarging to acquire a brain image B of enlarged gray matter through secondary dilation after primarily dilating the brain image A which includes the white matter, gray matter, and ventricles and in which the cranial dura mater is primarily removed in order to restore the brain image eroded;

second mask creating to create a second mask by multiplying the first mask and a cerebrospinal fluid mask, and acquire a brain image C of gray matter containing a portion of cerebrospinal fluid from the brain image B of enlarged gray matter using the second mask created;

gray matter acquiring to acquire a brain image F of gray matter through dilation and erosion after combining a brain image D including the white matter, gray matter, and ventricles acquired through erosion and dilation of the brain image C which includes the white matter, gray matter, and ventricles and in which the cranial dura mater is primarily removed with the brain image C of enlarged gray matter;

second dura removing to secondarily remove the cranial dura mater after acquiring a brain image G by subtracting other structures from the brain image F of gray matter, and then eroding and dilating the brain image G acquired; and segmented brain image acquiring to acquire a segmented brain image I in which structures other than the white matter, gray matter, cerebrospinal fluid, and ventricles are removed by post-processing to fill a hole in a brain image H from the second dura removing.

6. The method for segmenting brain in MRI images of claim 5, further comprising:

final brain image deriving to create a final mask by combining the masks for the respective brain components, and acquire a final brain image J, in which the cranial dura mater and a part below cerebellum are removed, from the segmented brain image I acquired and the preprocessed brain image using the final mask created.

7. A non-transitory recording medium on which a program for executing the method for segmenting brain in MRI images of claim 6 is recorded and executable on a computer.

8. The method for segmenting brain in MRI images of claim 5, wherein the first mask is provided to remove a brain image acquired using an other structure mask after multiplying a brain image of gray matter acquired using a gray matter mask by a constant greater than 1, and combining a brain image of a white matter acquired using a white mask with a brain image of ventricles acquired using a ventricular mask.

9. A non-transitory recording medium on which a program for executing the method for segmenting brain in MRI images of claim 8 is recorded and executable on a computer.

10. A non-transitory recording medium on which a program for executing the method for segmenting brain in MRI images of claim 5 is recorded and executable on a computer.

* * * * *